United States Patent
von Malmborg et al.

(10) Patent No.: US 8,038,628 B2
(45) Date of Patent: Oct. 18, 2011

(54) TORQUE DEVICE FOR A SENSOR GUIDE WIRE

(75) Inventors: Pär von Malmborg, Uppsala (SE); Pär Gustafsson, Uppsala (SE)

(73) Assignee: Radi Medical Systems AB, Uppsala (SE)

( * ) Notice: Subject to any disclaimer, the term of this patent is extended or adjusted under 35 U.S.C. 154(b) by 639 days.

(21) Appl. No.: 11/802,766

(22) Filed: May 24, 2007

(65) Prior Publication Data

US 2008/0294030 A1  Nov. 27, 2008

(51) Int. Cl.
*A61M 25/00* (2006.01)

(52) U.S. Cl. ........................ 600/585; 604/528

(58) Field of Classification Search ............... 226/127, 226/128; 600/433, 434, 585; 604/528
See application file for complete search history.

(56) References Cited

U.S. PATENT DOCUMENTS

| | | | |
|---|---|---|---|
| 5,240,437 A * | 8/1993 | Christian | 439/668 |
| 5,392,778 A * | 2/1995 | Horzewski | 600/434 |
| RE35,648 E | 11/1997 | Tenerz et al. | |
| 5,851,189 A * | 12/1998 | Forber | 600/585 |
| 5,938,624 A | 8/1999 | Akerfeldt et al. | |
| 6,061,588 A * | 5/2000 | Thornton et al. | 600/424 |
| 6,428,336 B1 | 8/2002 | Akerfeldt | |
| 6,533,772 B1 * | 3/2003 | Sherts et al. | 606/1 |
| 2005/0288632 A1 * | 12/2005 | Willard | 604/103.01 |
| 2008/0262432 A1 * | 10/2008 | Miller | 604/164.13 |

OTHER PUBLICATIONS

RADI Medical Systems, Drawing of Torque Device, Mar. 1998.
Qosina catalog, http://www.qosina.com/catalog/part.asp?partno=97327&k=torque&c=All&store=3, Qosina Corp. New York, NY, Jun. 8, 2006.
Qosina Catalog, http://www.qosina.com/catalog/part.asp?partno=97333&k=torque&c=All&store=5, Qosina Corp., New York, NY, Jun. 8, 2006.

* cited by examiner

*Primary Examiner* — Max Hindenburg
*Assistant Examiner* — Jonathan M Foreman
(74) *Attorney, Agent, or Firm* — Foley & Lardner LLP

(57) ABSTRACT

The invention relates to a torque device for a sensor guide wire having a sensor provided at a distal portion and a male connector provided at the proximal end, which torque device comprises a grip body and a cap adapted to be joined to the grip body, and a number of chuck segments provided on the cap or the grip body, wherein the torque device is a one-way device defining an insertion direction for the sensor guide wire and wherein the chuck segments have free ends which are directed in the insertion direction.

22 Claims, 4 Drawing Sheets

TORQUE DEVICE FOR A SENSOR GUIDE WIRE

FIELD OF THE INVENTION

The invention relates generally to sensors mounted on guide wires for intravascular measurements of physiological variables in a living body, and in particular to the design of a torque device which is attached to the guide wire and by which the sensor is maneuvered to a specific measurement site within the living body.

BACKGROUND OF THE INVENTION

Sensor and guide wire assemblies in which a sensor, adapted for measurements of physiological variables in a living body, such as blood pressure and temperature, is mounted at a distal portion of a guide wire are known.

For example, the U.S. Pat. No. Re. 35,648 (which is assigned to the present assignee and incorporated herein by reference for the devices and techniques disclosed therein) discloses a sensor and guide wire assembly comprising a sensor element, an electronic unit, signal transmitting cables connecting the sensor element to the electronic unit, a flexible tube having the signal cables and the sensor element disposed therein, a solid metal wire, and a coil attached to the distal end of the solid wire. The sensor element comprises a pressure sensitive device, e.g. a membrane, with piezoresistive elements electrically connected in a Wheatstone bridge-type of circuit arrangement mounted thereon.

The sensor guide wire ends proximally in a male connector, which is adapted for insertion into a corresponding female connector, to therefrom transmit the sensor signals to an external monitor device. In the U.S. Pat. No. 5,938,624 (which is assigned to the present assignee and incorporated herein by reference for the devices and techniques disclosed therein) an example of such a male connector is disclosed. This male connector comprises a core wire and conductive members spaced apart longitudinally along the core wire. Each conductive member is electrically connected to a signal cable, which is connected to the Wheatstone bridge circuit arranged at the sensor element in a distal portion of the sensor guide wire. The conductive members are electrically insulated from each other, and also from the core wire, by insulating material, which is disposed between the core wire and the conductive members as well as between the conductive members themselves, such that the insulating material has an outer surface which is coextensive with the outer surfaces of the conductive members, to facilitate both cleaning of the male connector and insertion of the male connector into an electrically and mechanically matching female connector.

Although not mandatory, the sensor guide wire is often maneuvered by the aid of a so-called torque device, which is movable along the sensor guide wire and which a doctor clamps around the guide wire at a proximal part thereof, to provide a good grip for the doctor as he or she is advancing the sensor guide wire through the cardiovascular system of a patient. Also an integrated portion of a female connector can be of a design similar to such a torque device; and the female connector can in this respect therefore be regarded as a torque device as it is capable of facilitating maneuvering of a sensor guide wire.

It can further be mentioned that corresponding torque devices also are used in connection with conventional (i.e. sensor-less) guide wires, but due to the delicate and sensitive design of a male connector, with its relatively thinner core wire and electrical connections between signal cables and conductive members, a sensor guide wire is particularly prone to damages during introduction of the male connector into the torque device, and the known torque devices are therefore not suitable for use together with a sensor guide wire.

Consequently, there is still a need for an improved torque device which obviates, or at least reduces, damage to a male connector, which is part of a sensor and guide wire assembly and which is introduced into or through the torque device.

SUMMARY OF THE INVENTION

Embodiments of the present invention are directed to a torque device adapted for use together with a sensor and guide wire assembly, which comprises a sensor element arranged in a distal portion of a sensor guide wire, whose proximal end is provided with a male connector.

In a first embodiment, the torque device is a separate device, which basically comprises a grip body and a cap. The cap comprises a threaded portion, which is adapted to be screwed into corresponding threads provided at an interior wall of the grip body, and a chuck part, which in turn comprises a number of recesses or notches to thereby create a corresponding number of clamps or chuck segments, which, when the cap is screwed into the grip body, are compressed and clamped around a portion of a sensor guide wire that has been introduced through the torque device. According to embodiments of the invention, the chuck segments, or rather the free ends of the chuck segments, are directed in the direction of insertion of a male connector which is part of a sensor guide wire. By this arrangement, the risk that the proximal end of the male connector during introduction accidentally deviates slightly from its intended central path and, instead of being passed through the chuck part, abuts the bottom of a notch is eliminated.

In a second embodiment of the present invention, the torque device is part of a female connector and constitutes an integrated part thereof.

Weakening sections can be provided between the chuck part and the threaded portion of a cap of a torque device, to thereby facilitate the compression of the chuck segments and provide a larger contact surface between the chuck segments and a sensor guide wire.

To ensure as large as possible contact surface and thereby an even distribution of contact pressure between the chuck segments and a sensor guide wire, each of the outer sides of the chuck segments can be provided with a shoulder, which, when the cap and grip part are screwed together, abuts a corresponding transition portion provided inside the grip part, as is described below for one embodiment of the present invention.

DETAILED DESCRIPTION OF PREFERRED EMBODIMENTS

Figure 1:
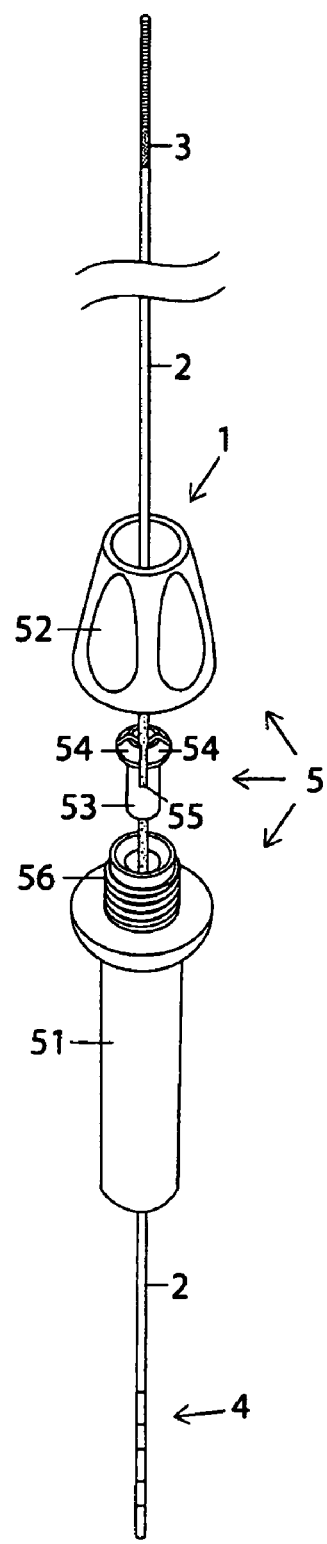
FIG. 1 is a schematic illustration of a sensor and guide wire assembly comprising a torque device according to prior art.

FIG. 1 illustrates schematically the essential parts of a sensor and guide wire assembly 1 comprising a sensor guide wire 2, a sensor element 3 provided in or at a distal portion of the sensor guide wire 2, a male connector 4 arranged at the proximal end of the sensor guide wire 2, and a torque device 5 disposed somewhere along the length of the sensor guide wire 2. With exception of the torque device 5, the sensor and guide wire assembly 1 can be regarded as a generic sensor and guide wire assembly, which also can be used in combination with the novel torque device in accordance with the present invention and described below.

To make it easier to appreciate the special advantages of the novel torque device according to the invention, the features of the known torque device 5 will be described in some detail in conjunction with FIG. 1. The torque device 5, which has a lumen adapted for reception of a sensor guide wire, comprises three parts: a grip portion 51, a cap 52, and a collet 53. The cap 52 is provided with internal threads (not visible in FIG. 1), which match corresponding external threads 56 provided on a portion of the grip portion 51, such that the grip portion 51 and the cap 52 can be screwed together. The collet 53 is a separate member, which, when the grip portion 51 and cap 52 are screwed together, is disposed within the torque device 5. As is apparent from FIG. 1, the collet 53 is provided with a number of chuck segments 54 interspaced by a corresponding number of notches 55.

The cap 52 constitutes the most distal part of the torque device 5. This means that a male connector, which, as part of a sensor guide wire, is introduced through the torque device 5, first enters the cap 52 and is subsequently passed through the grip portion 51. A notable feature of the known torque device 5 is therefore that the bottoms of the notches 55 are facing the approaching end of the male connector. This means that if the male connector would deviate slightly from its intended central course there is a potential risk that the end of the male connector hits the bottom of a notch 55, causing the male connector to be bent and—as a worst case—to be damaged and become more or less useless for its intended purpose.

Figure 2:
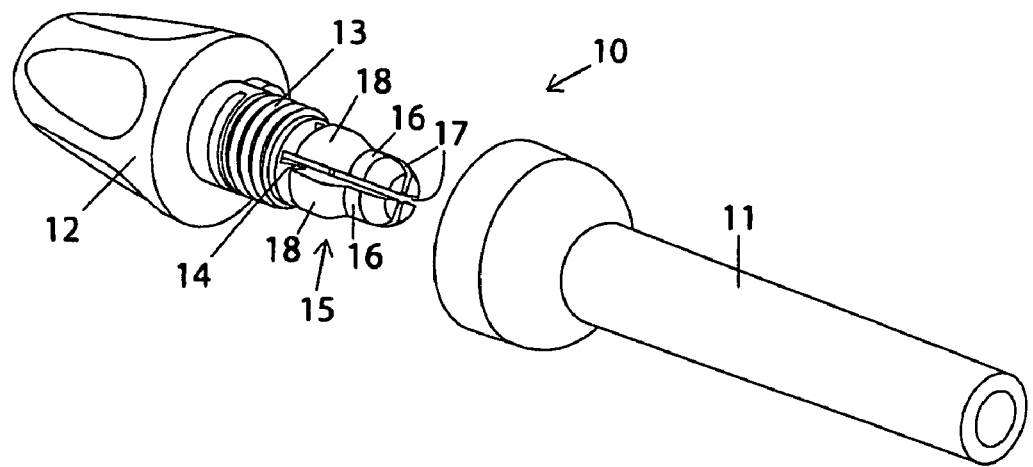
FIG. 2 illustrates a first embodiment of a torque device according to the present invention.

FIG. 2 illustrates a first embodiment of a torque device 10 according to the present invention. The torque device 10, which has a lumen adapted for reception of a sensor guide wire, comprises a grip body 11 and a cap 12, which has a threaded portion 13, a weakened section 14, and a chuck portion 15. The threads machined or otherwise provided in the threaded portion 13 match with internal threads (not visible in FIG. 2) provided inside the grip body 11, such that the grip body 11 and cap 12 can be screwed together. The chuck portion 15 comprises an arbitrary number of chuck segments 16, which are interspaced and created by a corresponding number of notches 17. When a male connector has been introduced through the torque device 10 such that the torque device 10 is placed somewhere along the length of an adjoining sensor guide wire, the grip body 11 and cap 12 are screwed together, causing the chuck segments to be compressed inwardly, to thereby clamp and fixate the torque device 10 on the sensor guide wire. In this preferred and exemplifying embodiment, the weakening section 14 is provided in order to facilitate the compression of the chuck portion 15 and to create a larger and more evenly distributed contact surface between the inner surface of the chuck segments 16 and the outer surface of the sensor guide wire. For similar reasons, each of the chuck segments 16 is provided with a shoulder 18, the function of which is described below. Optionally (and not shown in FIG. 2) the grip body 11 and/or the cap 12 can be provided with an arresting mechanism or arresting member, which prevents the grip body 11 and cap 12, once screwed together, from being unintentionally unscrewed.

In contrast to the known torque device 5 shown in FIG. 1, the chuck segments 16, i.e. the free ends thereof, are arranged in the direction of insertion of a male connector, i.e. the bottoms of the notches 17 do not face the end of a male connector being introduced into the torque device 10. The corresponding risk that the end of the male connector accidentally is steered into a notch 17 and therein encounters the bottom of the notch 17, with the accompanying risk of being bent and damaged, has thereby been eliminated. Here, it may be mentioned that for a conventional (i.e. sensor-less) guide wire, a slight bending of the proximal end of the guide wire usually is insignificant, but for a sensor and guide wire assembly arranged to accurately measure physiological and critical variables related to, for example, a patient's cardiovascular performance, the correct functioning of the sensor assembly is of outermost importance, and each type of mechanical and thereby electrical malfunction may have severe medical implications, or causes at least a prolongation of the medical operation at hand, with corresponding discomfort for the patient involved and additional costs.

As was indicated above, it is advantageous to create a large contact surface between the inner surfaces of the chuck segments of a torque device and the outer surface of a sensor guide wire introduced through the torque device. This effect can be further enhanced by providing the outer surfaces of the chuck segments with a shoulder, which matches a corresponding transition step provided within the grip body. These characteristics of a torque device according to an embodiment of the invention are most clearly seen in FIG. 3, where a cross-section of the torque device 10 of FIG. 2 is illustrated in a state just before the final joining of the grip body 11 and the cap 12. From FIG. 3 it should be clear that the chuck segments 16 with their shoulders 18 fit into corresponding transitions steps 19 provided in the interior of the grip body 11. It may further be appreciated that by these shoulders 18 and transition steps 19, the chuck segments 16 experience an almost parallel inward movement when the threaded portion 13 of the cap 12 is screwed into internal threads 22 provided in the interior of the grip body 11. (Without the shoulders 18 and transition steps 19, the displacement of the chuck segments 16 would at least initially be more like a rotational movement, with a tilting of the tips of the chuck segments 16.)

Figure 3:
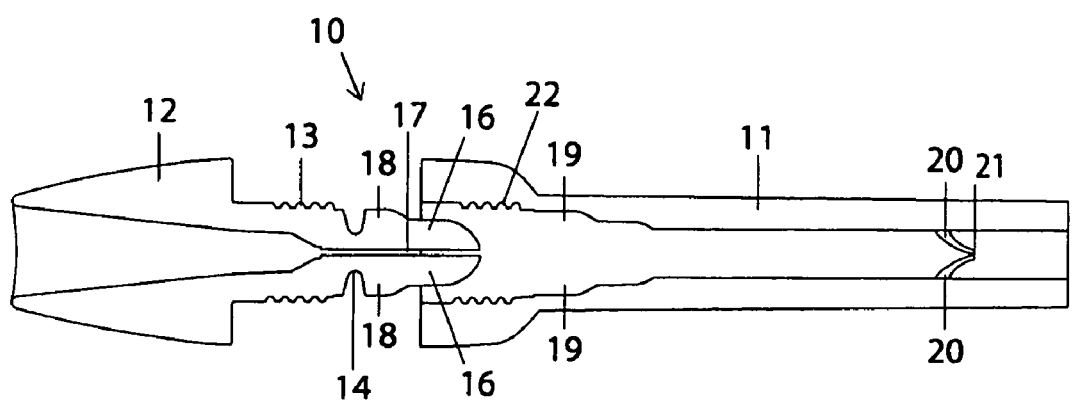
FIG. 3 represents a cross-section of the torque device of FIG. 2.

As stated above, a crucial characteristic of the torque device according to embodiments of the present invention is that the chuck segments, or rather the free ends of the chuck segments, are directed in the insertion direction of a male connector which is introduced into the torque device. To ensure correct insertion direction of the male connector, i.e. to ensure that a doctor does not introduce the sensor guide wire from the grip end of the torque device instead of from the cap end, the torque device 10 of FIG. 3 is provided with a pair of resilient lips 20. The lips 20 extend into the lumen of the torque device 10 and each of the lips 20 has a tip 21, which essentially is directed in the correct insertion direction of a male connector; and the tip 21 of one lip 20 is touching, or almost touching, the tip 21 of the opposite lip 20. From FIG. 3 it should therefore be apparent, that the resilient lips 20 give way for a male connector being inserted from the cap end of the torque device 10, but a male connector which is introduced from the opposite end, i.e. from the grip end, of the torque device 10 will encounter the tips 21 of the lips 20, and will consequently be prevented from further insertion.

Figure 5:
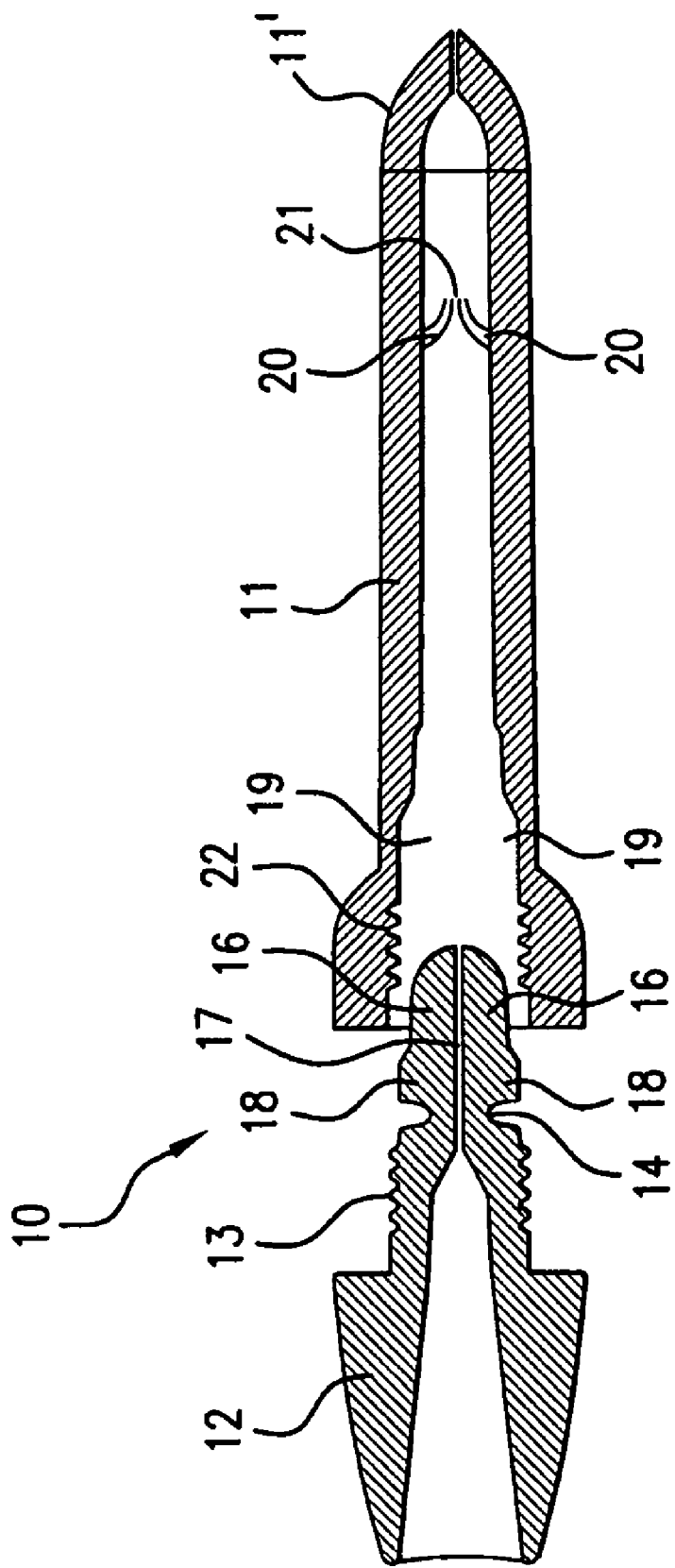
FIG. 5 illustrates a third embodiment of a torque device according to the present invention.

A torque device provided with lips as described above can accordingly be characterized as a one-way torque device. To ensure correct insertion direction for a torque device, other measures can however be taken. For example, the distal end of a cap can be provided with an end surface that bulges inwardly, to facilitate steering of a male connector into the torque device. On the other hand, the exit hole in the proximal end of a grip body can have a diameter which is adapted to the diameter of a sensor guide wire, and this exit hole can further be provided in a conical end surface 11' that bulges outwardly (as shown in FIG. 5), to make it difficult for a doctor to introduce a male connector from the grip end of a torque device. These distal and proximal end shapes are schematically indicated in FIG. 3. Similarly, the ends of the chuck segments can be chamfered, to obstruct introduction of a male connector from the grip end of a torque device. Despite the measures listed above, a torque device should generally be of such design that a doctor, based on his or her experience, intuitively knows the correct way of introducing a male connector into the torque device. In other words, a torque device should not have a symmetric shape, but should have a clearly defined grip part and a cap end, which promotes correct insertion of a male connector. In line with the above, the present invention is directed to a one-way torque device, wherein the term "one-way" is meant to encompass different functional features, ranging from mechanical measures, like resilient lips, that completely prevent a male connector from being introduced from the wrong end of the torque device, to structural measures, such as inward bulging of the distal cap end and outward bulging of the proximal grip end, that make it difficult to introduce a male connector from the wrong end of the torque device, to a general design that discourages a doctor from incorrect insertion of the male connector.

In the first embodiment of a torque device illustrated in FIGS. 2 and 3, the torque device is provided as a separate member, which is movable along the length of a sensor guide wire. As was indicated above, a torque device can also be provided as part of a female connector, into which the male connector of a sensor guide wire is to be inserted. From a certain aspect, the only difference between a separate torque device and a female connector is therefore that the former is movable along a sensor guide wire, and can be clamped at any position along the length of the sensor guide wire, whereas a female connector always is connected at a predetermined position, namely at the very proximal end of the sensor guide wire.

Figure 4:
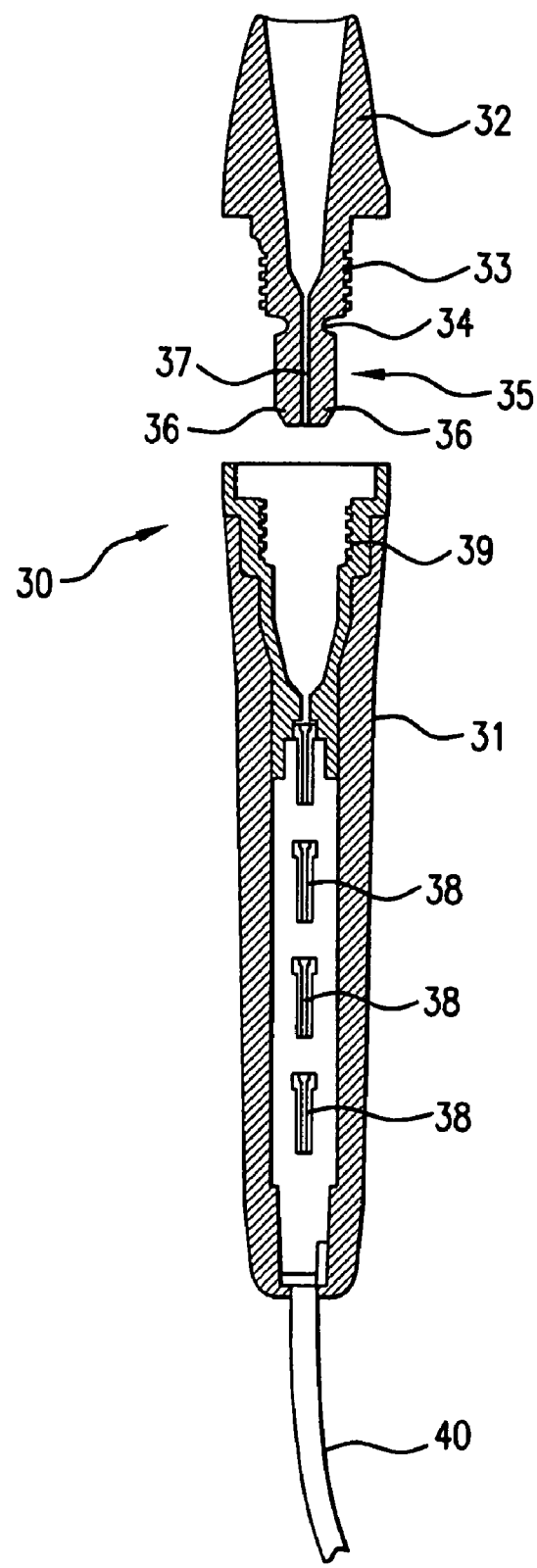
FIG. 4 illustrates a second embodiment of a torque device according to the present invention.

FIG. 4 illustrates a second embodiment of a torque device 30 according to the present invention. The torque device 30 comprises a grip body 31 and a cap 32, which has a threaded portion 33, a weakened section 34, and a chuck portion 35. The threads machined or otherwise provided in the threaded portion 33 match with internal threads 39 provided inside the grip body 31, such that the grip body 31 and cap 32 can be screwed together. The chuck portion 35 comprises an arbitrary number of chuck segments 36, which are interspaced and created by a corresponding number of notches 37. In this second embodiment, the grip body 31 does also constitute the actual female connector and has a number of electrically conductive members 38 provided therein, to mechanically and electrically match with a corresponding number of conductive members provided on a male connector. The conductive members 38 communicate with an external monitoring device via a cable 40, or via an antenna in or on body 31 which communicates via a wireless connection to an external monitoring device. Otherwise the torque device 30 functions in the same way as the previously described torque device 10, and in this respect the reader is referred to description above.

Although the present invention has been described with reference to specific embodiments, also shown in the appended drawings, it will be apparent for those skilled in the art that many variations and modifications can be done within the scope of the invention as described in the specification and defined with reference to the claims below. For example, it is possible to arrange a chuck portion of a torque device as part of a grip body, instead of as part of a cap, the essential feature being that the chuck segments are directed in the direction of insertion of a male connector being introduced into the torque device. Other changes that essentially only interchange a position of one particular member at the cap to a position at the grip body are also possible. The cap can, for example, be provided with internal threads while the grip body is provided with external threads. It is further possible to replace the threads by some other mechanism for joining the cap and grip body. A torque device can, for example, be provided with a bayonet mechanism.

What is claimed is:

1. A torque device having a lumen adapted for reception of a portion of a sensor guide wire, comprising:
    a grip body;
    a cap adapted to be joined to the grip body;
    a number of chuck segments provided on the cap or the grip body;
    wherein the torque device is a one-way device defining an intended insertion direction for the sensor guide wire and wherein the chuck segments have free ends which are directed in the insertion direction; and
    a mechanism configured to allow introduction of the sensor guide wire in the intended insertion direction and prevent introduction of the sensor guide wire in an opposite direction;
    wherein a proximal end of the cap is inserted into a distal end of the grip body.

2. A torque device according to claim 1, wherein the joining of the grip body and the cap is accomplished by a threaded portion which is provided on the cap and which matches with a threaded portion provided on the grip body.

3. A torque device according to claim 1, wherein the chuck segments are provided on the cap and wherein each of the chuck segments is provided with a shoulder that matches with a transition step provided inside the grip body.

4. A torque device according to claim 1, wherein the torque device has a lumen and comprises a pair of flexible lips, which extend into the lumen of the torque device and whose tips are directed essentially in the intended insertion direction, to allow introduction of the sensor guide wire in the intended insertion direction and prevent introduction of the sensor guide wire in the opposite direction.

5. A torque device according to claim 1, wherein the torque device is a separate device which is movable along the length of the sensor guide wire and which can be clamped and attached at an arbitrary position along the sensor guide wire.

6. A torque device according to claim 1, wherein the torque device constitutes a female connector adapted to accommodate a male connector provided at the proximal end of the sensor guide wire.

7. A torque device according to claim 1, wherein a weakened section adjoins to the chuck segments,
    wherein the weakened section has a smaller outer diameter than portions adjacent the weakened section in distal and proximal directions of the torque device.

8. A torque device according to claim 1, wherein a proximal end of the grip body includes a hole which is smaller than a hole in the distal end of the grip body.

9. A torque device having a lumen adapted for reception of a portion of a sensor guide wire, comprising:
    a grip body;
    a cap adapted to be joined to the grip body;
    a number of chuck segments provided on the cap;

wherein the torque device is a one-way device defining an intended insertion direction for the sensor guide wire and wherein the chuck segments have free ends which are directed in the insertion direction; and a mechanism configured to allow introduction of the sensor guide wire in the intended insertion direction and prevent introduction of the sensor guide wire in an opposite direction;

wherein a weakening section adjoins to the chuck segments, wherein the weakening section is a region where the cap has a smaller diameter than a threaded section of the cap.

10. A torque device according to claim 9, wherein the weakening section is separate and spaced a distance from an end of the cap.

11. A torque device according to claim 9, wherein the weakening section has a smaller outer diameter than portions adjacent the weakening section in distal and proximal directions of the cap.

12. A torque device according to claim 9, wherein a proximal end of the grip body includes a hole which is smaller than a hole in a distal end of the grip body.

13. A torque device having a lumen adapted for reception of a portion of a sensor guide wire, comprising:

a grip body;

a cap adapted to be joined to the grip body;

wherein the torque device is a one-way device having an intended insertion direction for the sensor guide wire; and a mechanism configured to allow introduction of the sensor guide wire in the intended insertion direction and prevent introduction of the sensor guide wire in an opposite direction;

wherein the cap and the grip body are configured such that when a proximal end of the cap is inserted into the grip body the proximal end of the cap is compressed.

14. A torque device according to claim 13, wherein the mechanism comprises at least one flexible lip whose tip is directed essentially in the intended insertion direction, to allow introduction of the sensor guide wire in the intended insertion direction and prevent introduction of the sensor guide wire in the opposite direction.

15. A torque device according to claim 13, wherein the torque device is a separate device which is movable along the length of the sensor guide wire and which can be clamped and attached at an arbitrary position along the sensor guide wire.

16. A torque device according to claim 13, further comprising a number of chuck segments on the cap, wherein a weakened section adjoins to the chuck segments, wherein the weakened section has a smaller outer diameter than portions adjacent the weakened section in distal and proximal directions of the torque device.

17. A torque device according to claim 13, wherein a proximal end of the grip body includes a hole which is smaller than a hole in a distal end of the grip body.

18. A torque device having a lumen adapted for reception of a portion of a sensor guide wire, comprising:

a grip body; and a cap adapted to be joined to the grip body;

wherein an extreme distal end of the cap has an opening of a first size which, moving from the extreme distal end toward a proximal end of the torque device, tapers to a second size which is smaller than the first size, and wherein an extreme proximal end of the grip body has an opening smaller in size than the first size and approximately equal in size to an outer diameter of the sensor guide wire, wherein a proximal end of the cap is inserted into an interior of a distal end of the grip body.

19. A torque device according to claim 18, wherein the torque device is a separate device which is movable along the length of the sensor guide wire and which can be clamped and attached at an arbitrary position along the sensor guide wire.

20. A torque device according to claim 18, wherein the extreme proximal end of the grip body includes an end surface that bulges outwardly in a proximal direction of the torque device.

21. A torque device according to claim 20, wherein the end surface is conical.

22. A torque device according to claim 18, wherein the proximal end of the cap is inserted into a lumen within the distal end of the grip body.

* * * * *